US009869629B1

(12) United States Patent
Ravi et al.

(10) Patent No.: US 9,869,629 B1
(45) Date of Patent: Jan. 16, 2018

(54) INNOVATIVE AND SAFE METHOD TO CONDUCT HIGH TEMPERATURE HALOGENATION OF METALLIC ALLOYS

(71) Applicant: Cal Poly Pomona Foundation, Inc., Pomona, CA (US)

(72) Inventors: Vilupanur A Ravi, Claremont, CA (US); Juan Carlos Nava, Upland, CA (US); Shahan Kasnakjian, Glendale, CA (US)

(73) Assignee: Cal Poly Pomona Foundation, Inc., Pomona, CA (US)

( * ) Notice: Subject to any disclaimer, the term of this patent is extended or adjusted under 35 U.S.C. 154(b) by 0 days.

(21) Appl. No.: 15/436,117

(22) Filed: Feb. 17, 2017

Related U.S. Application Data

(60) Provisional application No. 62/297,519, filed on Feb. 19, 2016.

(51) Int. Cl.
| | |
|---|---|
| *G01N 17/04* | (2006.01) |
| *G01N 17/00* | (2006.01) |
| *G01N 33/20* | (2006.01) |
| *C01G 53/09* | (2006.01) |
| *C01B 7/03* | (2006.01) |

(Continued)

(52) U.S. Cl.
CPC ............. *G01N 17/006* (2013.01); *C01B 7/03* (2013.01); *C01B 9/02* (2013.01); *C01G 53/09* (2013.01); *G01N 17/043* (2013.01); *G01N 33/0052* (2013.01); *G01N 17/00* (2013.01); *G01N 33/20* (2013.01); *Y10T 436/19* (2015.01); *Y10T 436/25875* (2015.01)

(58) Field of Classification Search
CPC .... G01N 33/0052; G01N 33/20; G01N 17/00; G01N 17/002; G01N 17/006; G01N 17/008; G01N 17/04; G01N 17/043; Y10T 436/19; Y10T 436/25875; C01G 53/09; C01B 7/03; C01B 9/02
USPC .......... 436/6, 73, 84, 124, 147, 181; 422/53, 422/558, 559
See application file for complete search history.

(56) References Cited

U.S. PATENT DOCUMENTS 2,956,225 A * 10/1960 Marsh .................... G01N 17/00
324/446
4,019,133 A * 4/1977 Manley .................. G01N 17/00
324/700

(Continued)

*Primary Examiner* — Maureen Wallenhorst
(74) *Attorney, Agent, or Firm* — Greenberg Traurig LLP

(57) ABSTRACT

The present invention discloses a method and system for conducting high temperature corrosion tests on metallic alloys without the need for extensive laboratory equipment and attendant safety measures through the use of a two-compartment ampoule where a vestibule connects these two compartments. A pre-selected mixture of salts is placed in one compartment in order to generate a specific partial pressure of halogen gas; and a metallic alloy is placed in the other compartment. The ampoule is then heated to a pre-determined temperature and held at this temperature for a pre-determined time period. A halogen gas of a specific partial pressure is thereby generated from the mixture of salts which comes into contact with the metallic alloy. Because the ampoule creates a sealed environment, the metallic alloy is under constant halogenation during the pre-determined time period. The metallic alloy is removed for examination when the pre-determined time period expires.

4 Claims, 1 Drawing Sheet

(51) Int. Cl.
 C01B 9/02 (2006.01)
 G01N 33/00 (2006.01)

(56) References Cited

U.S. PATENT DOCUMENTS

2012/0103105 A1* 5/2012 Butterfield ............... G01N 3/02
 73/799
2016/0041085 A1* 2/2016 England ............... G01N 17/043
 436/6

* cited by examiner

INNOVATIVE AND SAFE METHOD TO CONDUCT HIGH TEMPERATURE HALOGENATION OF METALLIC ALLOYS

RELATED APPLICATION

This application claims the benefit of priority under 35 U.S.C. § 119(e) to Provisional Application No. 62/297,519, filed on Feb. 19, 2016, which is incorporated by reference in its entirety.

STATEMENT REGARDING FEDERALLY SPONSORED RESEARCH OR DEVELOPMENT

Not Applicable.

INCORPORATION BY REFERENCE OF MATERIAL SUBMITTED ON A COMPACT DISC

Not Applicable.

THE NAMES OF THE PARTIES TO A JOINT RESEARCH AGREEMENT

Not applicable.

BACKGROUND OF THE INVENTION

Many metals readily react with halogen gases at elevated temperatures to form metal halides. Some metal halides exhibit low melting points and some even sublime at relatively low temperatures. As a result, metallic alloys that form metal halides may suffer high-temperature corrosion. Industrial environments often contain halogen gases. Therefore, reactor vessels that are resistant to high temperature halogenation attack are often required.

Hydrogen ($H_2$) and silicon-tetrachloride ($SiCl_4$) are used at temperatures between 950° to 1150° F. (or 510° to 621° C.) and at a relatively high pressure to produce solar grade silicon. The reaction between hydrogen and silicon-tetrachloride results in the formation of hydrochloric acid gas, HCl(g). The equilibrium between hydrogen gas and hydrochloric acid gas defines a partial pressure of chlorine gas ($P_{Cl2}$) that can lead to high temperature chloridation attack on reactor vessel which is usually made of metallic alloys. Therefore, there is a need to determine the extent of halogenation of metallic alloys in an environment containing halogen gases.

BRIEF SUMMARY OF THE INVENTION

Traditionally, metallurgical corrosion evaluation involves creating an accelerated simulated environment for corrosion testing using extensive laboratory equipment and constant monitoring to ensure safety. The present invention relates to a novel method and system for conducting high temperature corrosion tests on metallic alloys without the need for extensive laboratory equipment and attendant safety measures. The present invention comprises a two-compartment ampoule that provides a sealed environment for corrosion testing and using the halogen gas generated from a pre-selected salt mixture placed within the ampoule to simulate a halogen-containing environment a tested metallic alloy will be subject to. The present invention may be used for determining the corrosion rate of metallic alloys in halogen-containing environments.

It is an objective of this invention to provide a method for testing metallic alloys in a halogen-containing environment with ease and reduced safety concerns.

It is a further objective of this invention to provide a method that allows for long term exposure of metallic alloys in order to conduct testing of said metallic alloys in a halogen-containing environment.

These and other objectives are preferably accomplished by providing a method and system comprising a two-compartment sealed container (e.g., an ampoule) where a channel (e.g., a vestibule) connects these two compartments. A pre-selected mixture of salts (e.g., mixture of nickel (Ni) and nickel chloride ($NiCl_2$) is placed in one compartment in order to generate a specific partial pressure of halogen gas (e.g., chlorine gas); and a metallic alloy is placed in the other compartment. The ampoule is then heated to a pre-determined temperature and held at this temperature for a pre-determined time period (e.g., 250 to 1,000 hours). At the pre-determined temperature, a halogen gas (e.g., chlorine gas) of a specific partial pressure is generated from said mixture of salts, flows through the vestibule and comes into contact with said metallic alloy. The amount of the mixture should be sufficient to generate sufficient halogen gas for the duration of the pre-determined time period. Because the ampoule creates a sealed environment, the metallic alloy is under constant halogenation during the pre-determined time period. Upon expiration of the pre-determined time period, the metallic alloy is removed from the ampoule and examined in order to determine the results of halogenation of the metallic alloy.

These and other aspects of this invention will become apparent to those skilled in the art after reviewing the following description of the invention.

BRIEF DESCRIPTION OF THE SEVERAL VIEWS OF THE DRAWINGS

The above-mentioned features and objects of the present disclosure will become more apparent with reference to the following description taken in conjunction with the accompanying drawings and images wherein like reference numerals denote like elements and in which.

DETAILED DESCRIPTION OF THE INVENTION

For illustrative purposes, the principles of the present invention are described by referring to an exemplary embodiment thereof. Before any embodiment of the invention is explained in detail, it should be understood that the invention is not limited in its application to the details of construction and the arrangement of components set forth in the following description or illustrated in the following drawings. The invention is capable of other embodiments and of being practiced or of being carried out in various ways. Also, it should be understood that the phraseology and terminology used herein is for the purpose of description and should not be regarded as limiting. The use of "including," "comprising," or "having" and variations thereof herein is meant to encompass the items listed thereafter and equivalents thereof as well as additional items.

Figure 1:
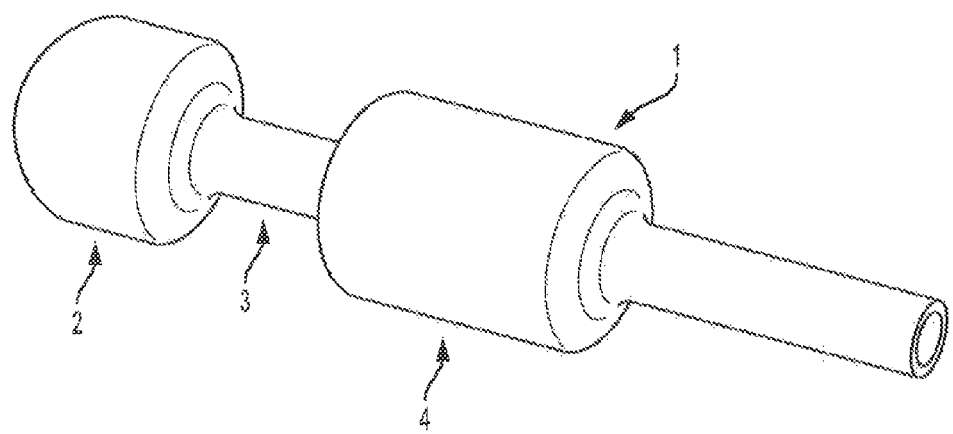
FIG. 1 is a perspective view of a two-compartment ampoule where a vestibule connects these two compartments.

The present invention involves exposing a metallic alloy to a halogen gas of a specific partial pressure at a pre-determined temperature over a pre-determined time period. Flowing gases can be used to set up the desired partial pressures in the atmosphere. However, these pose significant safety issues and require scrubbing systems. In the present invention, an innovative closed system was devised, thereby eliminating the necessity for an external, continuous flow system with its associated safety concerns. This innovation provided the necessary gaseous environment to which the metal or alloy was exposed while eliminating safety concerns. In one embodiment, as shown in FIG. 1, a sealed container 1, e.g., an ampoule, having two compartments (2 and 4) is disclosed. These two compartments (2 and 4) are connected via a channel 3, e.g., a vestibule. Fluids (gases or liquid) may flow freely between these two compartments. The sealed container 1 should be heat conductive. Preferably, the sealed container 1 is purged with an inert gas, such as argon. In some embodiments, the sealed container 1 is made of glass or quartz.

Figure 2:
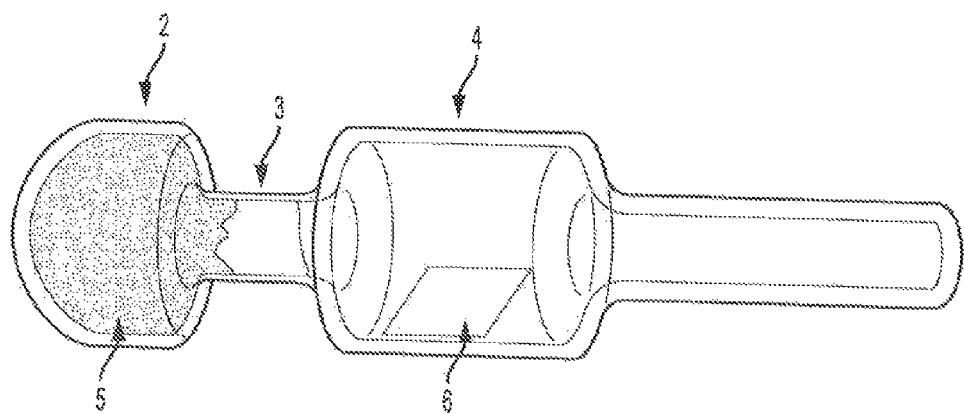
FIG. 2 is a perspective view of a two-compartment ampoule where a pre-selected mixture of salts is placed in one compartment and a metallic alloy coupon is placed in the other compartment.

In the present invention, as shown in FIG. 2, a pre-selected mixture of salts 5, which is capable of generating a halogen gas at equilibrium, is placed in one compartment 2. In one embodiment, the pre-selected mixture 5 comprises an equi-molar mixture of nickel (Ni) and nickel chloride ($NiCl_2$), which at equilibrium generates chlorine gas of a specific partial pressure according to the following thermodynamic equilibrium:

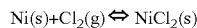

A metallic alloy element 6 is placed in the other compartment. In one embodiment, the metallic alloy element 6 is a metallic alloy coupon. The sealed container 1 containing the mixture 5 and the metallic alloy element 6 is then heated to a pre-determined temperature (e.g., 626° C.) and held at this temperature for a pre-determined time period (e.g., 100. 250, 1,000 hours, etc.). At the pre-determined temperature, a halogen gas (e.g., chlorine gas) of a specific partial pressure is generated from the mixture 5, which flows through the channel 3 and filled the entire sealed container 1. The amount of the mixture should be sufficient to generate sufficient halogen gas for the duration of the pre-determined time period. Therefore, the metallic alloy element 6 is constantly exposed to the halogen gas under the specific partial pressure during the entire pre-determined time period. Upon expiration of the pre-determined time period, the metallic alloy element 6 is then removed from the sealed container 1 and cleaned (e.g., by ultrasonic cleaning) in order to be examined and determine the results of halogenation (e.g., corrosion rate) of the metallic alloy element 6.

The metallic alloy element 6 may be analyzed in various ways including mass loss analysis and destructive metallography using optical and/or electron microscopy. In one embodiment, the mass weight of metallic alloy element 6 is recorded before exposing to the halogen gas in the sealed container 1. The mass weight of metallic alloy element 6 is again recorded after exposing to the halogen gas in the sealed container 1 and after being cleaned. The mass weight change of metallic alloy element 6 before and after exposing to the halogen gas is an indicator of the effect of halogenation on the tested metallic alloy.

The previous description of the disclosed examples is provided to enable any person of ordinary skill in the art to make or use the disclosed methods and apparatus. Various modifications to these examples will be readily apparent to those skilled in the art, and the principles defined herein may be applied to other examples without departing from the spirit or scope of the disclosed method and apparatus. The described embodiments are to be considered in all respects only as illustrative and not restrictive and the scope of the invention is, therefore, indicated by the appended claims rather than by the foregoing description. All changes which come within the meaning and range of equivalency of the claims are to be embraced within their scope. Skilled artisans may implement the described functionality in varying ways for each particular application, but such implementation decisions should not be interpreted as causing a departure from the scope of the disclosed apparatus and methods. The steps of the method or algorithm may also be performed in an alternate order from those provided in the examples.

The invention claimed is:

1. A method for conducting halogenation of metallic alloys comprising:
    providing a sealed container wherein the sealed container comprises a first compartment, a second compartment, and a channel that connects the first compartment and the second compartment wherein the channel is configured to allow gas flowing between the first and second compartments;
    enclosing a metallic alloy element in the first compartment;
    enclosing a pre-selected mixture of salts comprises nickel and nickel chloride in the second compartment;
    heating the sealed container to a pre-determined temperature and maintaining at the pre-determined temperature for a pre-determined time period so that the pre-selected mixture of salts generate a chlorine gas of a specific partial pressure at the pre-determined temperature;
    exposing the metallic alloy element to the chlorine gas that is generated from the pre-selected mixture of salts and flowing from the second compartment for the pre-determined time period;
    the pre-determined temperature is approximately 626 degrees Celsius (626° C.); and
    the pre-determined time period is within a range of approximately 250 to 1000 hours.

2. The method of conducting halogenation of metallic alloys of claim 1 wherein the sealed container is a sealed capsule made of quartz.

3. The method of conducting halogenation of metallic alloys of claim 1 further comprising:
    determining a first mass weight of the metallic alloy element before the metallic alloy element is exposed to the chlorine gas generated from the pre-selected mixture of salts;
    determining a second mass weight of the metallic alloy element after the metallic alloy element has been exposed to the chlorine gas generated from the pre-selected mixture of salts for the pre-determined time period.

4. The method of conducting halogenation of metallic alloys of claim 3 further comprising:
    determining a corrosion rate of the metallic alloy element based on the difference between the first mass weight and the second mass weight of the metallic alloy element for the pre-determined time period.

* * * * *